US009585669B2

(12) United States Patent
Becking et al.

(10) Patent No.: US 9,585,669 B2
(45) Date of Patent: *Mar. 7, 2017

(54) MULTIPLE LAYER FILAMENTARY DEVICES FOR TREATMENT OF VASCULAR DEFECTS

(75) Inventors: Frank P. Becking, Palo Alto, CA (US); Arturo S. Rosqueta, San Jose, CA (US); Siddharth Loganathan, Santa Clara, CA (US)

(73) Assignee: Covidien LP, Mansfield, MA (US)

(*) Notice: Subject to any disclaimer, the term of this patent is extended or adjusted under 35 U.S.C. 154(b) by 1125 days.

This patent is subject to a terminal disclaimer.

(21) Appl. No.: 13/470,013

(22) Filed: May 11, 2012

(65) Prior Publication Data
US 2012/0316598 A1 Dec. 13, 2012

Related U.S. Application Data

(63) Continuation of application No. 12/911,034, filed on Oct. 25, 2010, now Pat. No. 9,039,726, which is a
(Continued)

(51) Int. Cl.
*A61M 29/00* (2006.01)
*A61B 17/12* (2006.01)
(Continued)

(52) U.S. Cl.
CPC .... *A61B 17/12022* (2013.01); *A61B 17/1215* (2013.01); *A61B 17/12109* (2013.01);
(Continued)

(58) Field of Classification Search
CPC ........ A61B 17/12022; A61B 17/12172; A61B 17/12113; A61B 2017/00867; A61B 2017/12054; A61B 17/0057
See application file for complete search history.

(56) References Cited

U.S. PATENT DOCUMENTS 3,108,593 A 10/1963 Glassman
4,425,908 A 1/1984 Simon
(Continued)

FOREIGN PATENT DOCUMENTS

CA 2607529 4/2008
CN 101472537 A 7/2009
(Continued)

OTHER PUBLICATIONS

Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.
(Continued)

*Primary Examiner* — Diane Yabut
*Assistant Examiner* — Martin T Ton
(74) *Attorney, Agent, or Firm* — Mark J. Kertz, Esq.

(57) ABSTRACT

Braid-balls suitable for aneurysm occlusion and/or parent vessel occlusion/sacrifice (e.g., in treating neurovascular defects) are disclosed. Especially for aneurysm treatment, but also for either one of the aforementioned treatments, the form of the ball is very important. In particular, the density of the device is paramount in applications where braid itself is intended to moderate or stop blood flow—allowing thrombosis within a volume formed by the ball.

13 Claims, 3 Drawing Sheets

Related U.S. Application Data continuation of application No. 12/427,620, filed on Apr. 21, 2009, now Pat. No. 8,142,456.

(60) Provisional application No. 61/046,594, filed on Apr. 21, 2008, provisional application No. 61/046,670, filed on Apr. 21, 2008, provisional application No. 61/083,957, filed on Jul. 28, 2008, provisional application No. 61/083,961, filed on Jul. 28, 2008, provisional application No. 61/145,097, filed on Jan. 15, 2009.

(51) Int. Cl.
*A61M 29/02* (2006.01)
*A61B 17/00* (2006.01)
*A61B 18/00* (2006.01)

(52) U.S. Cl.
CPC .. *A61B 17/12113* (2013.01); *A61B 17/12118* (2013.01); *A61B 17/12172* (2013.01); *A61M 29/02* (2013.01); *A61B 2017/00526* (2013.01); *A61B 2017/00867* (2013.01); *A61B 2017/1205* (2013.01); *A61B 2017/12054* (2013.01); *A61B 2017/12068* (2013.01); *A61B 2018/00416* (2013.01); *Y10T 156/1051* (2015.01)

(56) References Cited

U.S. PATENT DOCUMENTS

| | | |
|---|---|---|
| 4,619,246 A | 10/1986 | Molgaard-Nielsen et al. |
| 4,655,771 A | 4/1987 | Wallsten |
| 4,768,507 A | 9/1988 | Fischell et al. |
| 4,921,484 A | 5/1990 | Hillstead |
| 4,998,539 A | 3/1991 | Delsanti |
| 5,026,377 A | 6/1991 | Burton et al. |
| 5,061,275 A | 10/1991 | Wallsten et al. |
| 5,064,435 A | 11/1991 | Porter |
| 5,104,404 A | 4/1992 | Wolff |
| 5,122,136 A | 6/1992 | Guglielmi et al. |
| 5,158,548 A | 10/1992 | Lau et al. |
| 5,222,971 A | 6/1993 | Willard et al. |
| 5,250,071 A | 10/1993 | Palermo |
| 5,334,210 A | 8/1994 | Gianturco |
| 5,378,239 A | 1/1995 | Termin et al. |
| 5,405,379 A | 4/1995 | Lane |
| 5,425,984 A | 6/1995 | Kennedy et al. |
| 5,499,981 A | 3/1996 | Kordis |
| 5,527,338 A | 6/1996 | Purdy |
| 5,545,208 A | 8/1996 | Wolff et al. |
| 5,545,209 A | 8/1996 | Roberts et al. |
| 5,549,635 A | 8/1996 | Solar |
| 5,624,461 A | 4/1997 | Mariant |
| 5,634,942 A | 6/1997 | Chevillon et al. |
| 5,645,558 A | 7/1997 | Horton |
| 5,662,703 A | 9/1997 | Yurek et al. |
| 5,690,671 A | 11/1997 | McGurk et al. |
| 5,702,419 A | 12/1997 | Berry et al. |
| 5,713,907 A | 2/1998 | Hogendijk et al. |
| 5,725,552 A | 3/1998 | Kotula et al. |
| 5,728,906 A | 3/1998 | Eguchi et al. |
| 5,733,294 A | 3/1998 | Forber et al. |
| 5,741,333 A | 4/1998 | Frid |
| 5,749,891 A | 5/1998 | Ken et al. |
| 5,749,919 A | 5/1998 | Blanc |
| 5,749,920 A | 5/1998 | Quiachon et al. |
| 5,766,151 A | 6/1998 | Valley et al. |
| 5,814,062 A | 9/1998 | Sepetka et al. |
| 5,830,230 A | 11/1998 | Berryman et al. |
| 5,846,261 A | 12/1998 | Kotula et al. |
| 5,853,422 A | 12/1998 | Huebsch et al. |
| 5,855,578 A | 1/1999 | Guglielmi et al. |
| 5,879,366 A | 3/1999 | Shaw et al. |
| 5,908,435 A | 6/1999 | Samuels |
| 5,911,731 A | 6/1999 | Pham et al. |
| 5,916,235 A | 6/1999 | Guglielmi |
| 5,925,060 A | 7/1999 | Forber |
| 5,928,228 A | 7/1999 | Kordis et al. |
| 5,928,260 A | 7/1999 | Chin et al. |
| 5,935,148 A | 8/1999 | Villar et al. |
| 5,935,362 A | 8/1999 | Petrick |
| 5,941,249 A | 8/1999 | Maynard |
| 5,944,738 A | 8/1999 | Amplatz et al. |
| 5,951,599 A | 9/1999 | McCrory |
| 5,957,948 A | 9/1999 | Mariant |
| 5,976,162 A | 11/1999 | Doan et al. |
| 5,980,554 A | 11/1999 | Lenker et al. |
| 6,001,092 A | 12/1999 | Mirigian et al. |
| 6,010,517 A | 1/2000 | Baccaro |
| 6,024,756 A | 2/2000 | Huebsch et al. |
| 6,033,423 A | 3/2000 | Ken et al. |
| 6,036,720 A | 3/2000 | Abrams et al. |
| 6,059,813 A | 5/2000 | Vrba et al. |
| 6,063,070 A | 5/2000 | Eder |
| 6,086,577 A | 7/2000 | Ken et al. |
| 6,093,199 A | 7/2000 | Brown et al. |
| 6,096,034 A | 8/2000 | Kupiecki et al. |
| 6,096,073 A | 8/2000 | Webster et al. |
| 6,099,526 A | 8/2000 | Whayne et al. |
| 6,106,530 A | 8/2000 | Harada |
| 6,110,191 A | 8/2000 | Dehdashtian et al. |
| 6,123,715 A | 9/2000 | Amplatz |
| 6,152,144 A | 11/2000 | Lesh et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,183,495 B1 | 2/2001 | Lenker et al. |
| 6,190,402 B1 | 2/2001 | Horton et al. |
| 6,193,708 B1 | 2/2001 | Ken et al. |
| 6,221,086 B1 | 4/2001 | Forber |
| 6,261,305 B1 | 7/2001 | Marotta et al. |
| 6,280,412 B1 | 8/2001 | Pederson, Jr. et al. |
| 6,306,141 B1 | 10/2001 | Jervis |
| 6,309,367 B1 | 10/2001 | Boock |
| 6,322,576 B1 | 11/2001 | Wallace et al. |
| 6,325,820 B1 | 12/2001 | Khosravi et al. |
| 6,331,184 B1 | 12/2001 | Abrams |
| 6,332,576 B1 | 12/2001 | Colley et al. |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,361,558 B1 | 3/2002 | Hieshima et al. |
| 6,375,668 B1 | 4/2002 | Gifford et al. |
| 6,379,372 B1 | 4/2002 | Dehdashtian et al. |
| 6,391,037 B1 | 5/2002 | Greenhalgh |
| 6,409,750 B1 | 6/2002 | Hyodoh et al. |
| 6,428,558 B1 | 8/2002 | Jones et al. |
| 6,443,972 B1 | 9/2002 | Bosma et al. |
| 6,447,531 B1 | 9/2002 | Amplatz |
| 6,454,780 B1 | 9/2002 | Wallace |
| 6,506,204 B2 | 1/2003 | Mazzocchi |
| 6,511,468 B1 | 1/2003 | Cragg et al. |
| 6,530,934 B1 | 3/2003 | Jacobsen et al. |
| 6,544,278 B1 | 4/2003 | Vrba et al. |
| 6,547,804 B2 | 4/2003 | Porter et al. |
| 6,551,303 B1 | 4/2003 | Van Tassel et al. |
| 6,569,179 B2 | 5/2003 | Teoh et al. |
| 6,579,302 B2 | 6/2003 | Duerig et al. |
| 6,579,303 B2 | 6/2003 | Amplatz |
| 6,585,756 B1 | 7/2003 | Strecker |
| 6,589,256 B2 | 7/2003 | Forber |
| 6,592,605 B2 | 7/2003 | Lenker et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,551 B1 | 8/2003 | Sullivan et al. |
| 6,613,074 B1 | 9/2003 | Mitelberg et al. |
| 6,626,939 B1 | 9/2003 | Burnside et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,652,555 B1 | 11/2003 | VanTassel et al. |

(56) References Cited

U.S. PATENT DOCUMENTS

| | | |
|---|---|---|
| 6,652,556 B1 | 11/2003 | VanTassel et al. |
| 6,666,882 B1 | 12/2003 | Bose et al. |
| 6,666,883 B1 | 12/2003 | Seguin et al. |
| 6,669,717 B2 | 12/2003 | Marotta et al. |
| 6,669,721 B1 | 12/2003 | Bose et al. |
| 6,676,696 B1 | 1/2004 | Marotta et al. |
| 6,682,505 B2 | 1/2004 | Bates et al. |
| 6,682,546 B2 | 1/2004 | Amplatz |
| 6,689,150 B1 | 2/2004 | VanTassel et al. |
| 6,689,486 B2 | 2/2004 | Ho et al. |
| 6,695,876 B1 | 2/2004 | Marotta et al. |
| 6,698,877 B2 | 3/2004 | Urlaub et al. |
| 6,699,274 B2 | 3/2004 | Stinson |
| 6,709,465 B2 | 3/2004 | Mitchell et al. |
| 6,712,835 B2 | 3/2004 | Mazzocchi et al. |
| 6,723,112 B2 | 4/2004 | Ho et al. |
| 6,723,116 B2 | 4/2004 | Taheri |
| 6,730,108 B2 | 5/2004 | Van Tassel et al. |
| 6,746,890 B2 | 6/2004 | Gupta et al. |
| 6,780,196 B2 | 8/2004 | Chin et al. |
| 6,792,979 B2 | 9/2004 | Konya et al. |
| 6,797,083 B2 | 9/2004 | Peterson |
| 6,802,851 B2 | 10/2004 | Jones et al. |
| RE38,653 E | 11/2004 | Igaki et al. |
| 6,811,560 B2 | 11/2004 | Jones et al. |
| 6,855,153 B2 | 2/2005 | Saadat |
| 6,855,154 B2 | 2/2005 | Abdel-Gawwad |
| RE38,711 E | 3/2005 | Igaki et al. |
| 6,860,893 B2 | 3/2005 | Wallace et al. |
| 6,936,055 B1 | 8/2005 | Ken et al. |
| 6,949,103 B2 | 9/2005 | Mazzocchi et al. |
| 6,949,113 B2 | 9/2005 | Van Tassel et al. |
| 6,953,472 B2 | 10/2005 | Palmer et al. |
| 6,979,341 B2 | 12/2005 | Scribner et al. |
| 6,989,019 B2 | 1/2006 | Mazzocchi et al. |
| 6,994,092 B2 | 2/2006 | van der Burg et al. |
| 6,994,717 B2 * | 2/2006 | Konya ............ A61B 17/12022 606/200 |
| 7,011,671 B2 | 3/2006 | Welch |
| 7,018,401 B1 | 3/2006 | Hyodoh et al. |
| 7,029,487 B2 | 4/2006 | Greene, Jr. et al. |
| 7,033,375 B2 | 4/2006 | Mazzocchi et al. |
| 7,048,752 B2 | 5/2006 | Mazzocchi et al. |
| 7,063,679 B2 | 6/2006 | Maguire et al. |
| 7,070,607 B2 | 7/2006 | Murayama et al. |
| 7,070,609 B2 | 7/2006 | West |
| 7,083,632 B2 | 8/2006 | Avellanet et al. |
| 7,128,073 B1 | 10/2006 | van der Burg et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,211,109 B2 | 5/2007 | Thompson |
| 7,229,461 B2 | 6/2007 | Chin et al. |
| 7,232,461 B2 | 6/2007 | Ramer |
| 7,244,267 B2 | 7/2007 | Huter et al. |
| 7,261,720 B2 | 8/2007 | Stevens et al. |
| 7,303,571 B2 | 12/2007 | Makower et al. |
| 7,306,622 B2 | 12/2007 | Jones et al. |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,393,358 B2 | 7/2008 | Malewicz |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,575,590 B2 | 8/2009 | Watson |
| 7,597,704 B2 | 10/2009 | Frazier et al. |
| 7,608,088 B2 | 10/2009 | Jones et al. |
| 7,621,928 B2 | 11/2009 | Thramann et al. |
| 7,632,296 B2 | 12/2009 | Malewicz |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,682,390 B2 | 3/2010 | Seguin |
| 7,691,124 B2 | 4/2010 | Balgobin |
| 7,695,488 B2 | 4/2010 | Berenstein et al. |
| 7,699,056 B2 | 4/2010 | Tran et al. |
| 7,727,189 B2 | 6/2010 | VanTassel et al. |
| 7,744,583 B2 | 6/2010 | Seifert et al. |
| 7,744,652 B2 | 6/2010 | Morsi |
| 7,763,011 B2 | 7/2010 | Ortiz et al. |
| 7,828,815 B2 | 11/2010 | Mazzocchi et al. |
| 7,828,816 B2 | 11/2010 | Mazzocchi et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| 7,993,364 B2 | 8/2011 | Morsi |
| RE42,758 E | 9/2011 | Ken et al. |
| 8,016,869 B2 | 9/2011 | Nikolchev |
| 8,016,872 B2 | 9/2011 | Parker |
| 8,062,379 B2 | 11/2011 | Morsi |
| 8,075,585 B2 | 12/2011 | Lee et al. |
| 8,142,456 B2 | 3/2012 | Rosqueta et al. |
| 8,202,280 B2 | 6/2012 | Richter |
| 8,221,445 B2 | 7/2012 | van Tassel et al. |
| 8,261,648 B1 | 9/2012 | Marchand et al. |
| 8,298,257 B2 | 10/2012 | Sepetka et al. |
| 8,430,012 B1 | 4/2013 | Marchand et al. |
| 8,454,681 B2 | 6/2013 | Holman et al. |
| 2001/0000797 A1 | 5/2001 | Mazzocchi |
| 2001/0007082 A1 | 7/2001 | Dusbabek et al. |
| 2001/0012949 A1 | 8/2001 | Forber |
| 2001/0051822 A1 | 12/2001 | Stack et al. |
| 2002/0013599 A1 | 1/2002 | Limon et al. |
| 2002/0013618 A1 | 1/2002 | Marotta et al. |
| 2002/0042628 A1 | 4/2002 | Chin et al. |
| 2002/0062091 A1 | 5/2002 | Jacobsen et al. |
| 2002/0111647 A1 | 8/2002 | Khairkhahan et al. |
| 2002/0165572 A1 | 11/2002 | Saadat |
| 2002/0169473 A1 | 11/2002 | Sepetka et al. |
| 2003/0004538 A1 | 1/2003 | Secrest et al. |
| 2003/0028209 A1 | 2/2003 | Teoh et al. |
| 2003/0057156 A1 | 3/2003 | Peterson et al. |
| 2003/0171739 A1 | 9/2003 | Murphy et al. |
| 2003/0171770 A1 | 9/2003 | Kusleika et al. |
| 2003/0176884 A1 | 9/2003 | Berrada et al. |
| 2003/0195553 A1 | 10/2003 | Wallace et al. |
| 2003/0199913 A1 | 10/2003 | Dubrul et al. |
| 2003/0199919 A1 * | 10/2003 | Palmer ............ A61B 17/12022 606/200 |
| 2004/0015224 A1 | 1/2004 | Armstrong et al. |
| 2004/0034386 A1 | 2/2004 | Fulton et al. |
| 2004/0044391 A1 | 3/2004 | Porter |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0106977 A1 | 6/2004 | Sullivan et al. |
| 2004/0111112 A1 | 6/2004 | Hoffmann |
| 2004/0122467 A1 | 6/2004 | VanTassel et al. |
| 2004/0122468 A1 | 6/2004 | Yodfat et al. |
| 2004/0143239 A1 | 7/2004 | Zhou et al. |
| 2004/0143286 A1 | 7/2004 | Johnson et al. |
| 2004/0153119 A1 | 8/2004 | Kusleika et al. |
| 2004/0162606 A1 | 8/2004 | Thompson |
| 2004/0172056 A1 | 9/2004 | Guterman et al. |
| 2004/0172121 A1 | 9/2004 | Eidenschink et al. |
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215229 A1 | 10/2004 | Coyle |
| 2004/0215332 A1 | 10/2004 | Frid |
| 2004/0249408 A1 | 12/2004 | Murphy et al. |
| 2004/0267346 A1 | 12/2004 | Shelso |
| 2005/0010281 A1 | 1/2005 | Yodfat et al. |

(56) References Cited

U.S. PATENT DOCUMENTS

| | | |
|---|---|---|
| 2005/0021077 A1 | 1/2005 | Chin et al. |
| 2005/0033408 A1 | 2/2005 | Jones et al. |
| 2005/0033409 A1 | 2/2005 | Burke et al. |
| 2005/0043759 A1 | 2/2005 | Chanduszko |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0222605 A1 | 10/2005 | Greenhalgh et al. |
| 2005/0228434 A1 | 10/2005 | Amplatz et al. |
| 2005/0267568 A1 | 12/2005 | Berez et al. |
| 2005/0273135 A1 | 12/2005 | Chanduszko et al. |
| 2005/0288763 A1 | 12/2005 | Andreas et al. |
| 2006/0052816 A1 | 3/2006 | Bates et al. |
| 2006/0074475 A1 | 4/2006 | Gumm |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0206199 A1 | 9/2006 | Churchwell et al. |
| 2006/0206200 A1 | 9/2006 | Garcia et al. |
| 2006/0217799 A1 | 9/2006 | Mailander et al. |
| 2006/0229700 A1 | 10/2006 | Acosta et al. |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0282152 A1 | 12/2006 | Beyerlein et al. |
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0050017 A1 | 3/2007 | Sims et al. |
| 2007/0088387 A1 | 4/2007 | Eskridge et al. |
| 2007/0093889 A1 | 4/2007 | Wu et al. |
| 2007/0100415 A1 | 5/2007 | Licata et al. |
| 2007/0106311 A1 | 5/2007 | Wallace et al. |
| 2007/0135826 A1 | 6/2007 | Zaver et al. |
| 2007/0150045 A1 | 6/2007 | Ferrera |
| 2007/0162104 A1 | 7/2007 | Frid |
| 2007/0173928 A1 | 7/2007 | Morsi |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233224 A1 | 10/2007 | Leynov et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2007/0293935 A1 | 12/2007 | Olsen et al. |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0051705 A1 | 2/2008 | Von Oepen et al. |
| 2008/0058856 A1 | 3/2008 | Ramaiah et al. |
| 2008/0065141 A1 | 3/2008 | Holman et al. |
| 2008/0065145 A1 | 3/2008 | Carpenter |
| 2008/0097495 A1 | 4/2008 | Feller, III et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0125848 A1 | 5/2008 | Kusleika et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0243226 A1 | 10/2008 | Fernandez et al. |
| 2008/0249562 A1 | 10/2008 | Cahill |
| 2008/0262598 A1 | 10/2008 | Elmaleh |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De La Mora Levy et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0125094 A1 | 5/2009 | Rust |
| 2009/0143849 A1 | 6/2009 | Ozawa et al. |
| 2009/0143851 A1 | 6/2009 | Paul, Jr. |
| 2009/0198315 A1 | 8/2009 | Boudjemline |
| 2009/0204145 A1 | 8/2009 | Matthews |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0259202 A1 | 10/2009 | Leeflang et al. |
| 2009/0264914 A1 | 10/2009 | Riina et al. |
| 2009/0275974 A1 | 11/2009 | Marchand et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2009/0318948 A1 | 12/2009 | Linder et al. |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030200 A1 | 2/2010 | Strauss et al. |
| 2010/0030220 A1 | 2/2010 | Truckai et al. |
| 2010/0036390 A1 | 2/2010 | Gumm |
| 2010/0042133 A1 | 2/2010 | Ramzipoor et al. |
| 2010/0069948 A1 | 3/2010 | Veznedaroglu et al. |
| 2010/0087908 A1 | 4/2010 | Hilaire et al. |
| 2010/0094335 A1 | 4/2010 | Gerberding et al. |
| 2010/0131002 A1 | 5/2010 | Connor et al. |
| 2010/0152767 A1 | 6/2010 | Greenhalgh et al. |
| 2010/0185271 A1 | 7/2010 | Zhang |
| 2010/0222802 A1 | 9/2010 | Gillespie, Jr. et al. |
| 2010/0249894 A1 | 9/2010 | Oba et al. |
| 2010/0256667 A1 | 10/2010 | Ashby et al. |
| 2010/0268260 A1 | 10/2010 | Riina et al. |
| 2010/0274276 A1 | 10/2010 | Chow et al. |
| 2010/0312270 A1 | 12/2010 | McGuckin, Jr. et al. |
| 2010/0331948 A1 | 12/2010 | Turovskiy et al. |
| 2011/0022149 A1 | 1/2011 | Cox et al. |
| 2011/0054519 A1 | 3/2011 | Neuss |
| 2011/0082493 A1 | 4/2011 | Samson et al. |
| 2011/0106234 A1 | 5/2011 | Grandt |
| 2011/0144669 A1 | 6/2011 | Becking et al. |
| 2011/0152993 A1 | 6/2011 | Marchand et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0245862 A1 | 10/2011 | Dieck et al. |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |

(56) References Cited

U.S. PATENT DOCUMENTS

| | | |
|---|---|---|
| 2012/0041470 A1 | 2/2012 | Shrivastava et al. |
| 2012/0065720 A1 | 3/2012 | Strauss et al. |
| 2012/0101561 A1 | 4/2012 | Porter |
| 2012/0143237 A1 | 6/2012 | Cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0226343 A1 | 9/2012 | Vo et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2013/0018451 A1 | 1/2013 | Grabowski et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0245670 A1 | 9/2013 | Fan |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304179 A1 | 11/2013 | Bialas et al. |
| 2013/0345739 A1 | 12/2013 | Brady et al. |
| 2014/0005713 A1 | 1/2014 | Bowman |

FOREIGN PATENT DOCUMENTS

| | | |
|---|---|---|
| DE | 1283434 B | 11/1968 |
| DE | 102008028308 | 4/2009 |
| DE | 102010050569 A1 | 5/2012 |
| DE | 102011011510 A1 | 8/2012 |
| EP | 743047 A2 | 11/1996 |
| EP | 775470 | 5/1997 |
| EP | 855170 A2 | 7/1998 |
| EP | 1621148 | 2/2006 |
| EP | 1637176 | 3/2006 |
| EP | 1752112 | 2/2007 |
| EP | 1942972 | 7/2008 |
| EP | 1872742 B1 | 5/2009 |
| EP | 2279023 A2 | 2/2011 |
| EP | 2363075 | 9/2011 |
| EP | 2496299 A2 | 9/2012 |
| EP | 2675402 A2 | 12/2013 |
| FR | 2556210 B1 | 4/1988 |
| FR | 2890306 | 3/2007 |
| JP | 11-506686 | 6/1999 |
| JP | 2003520103 A | 7/2003 |
| JP | 2003-524434 A | 8/2003 |
| JP | 2004-049585 A | 2/2004 |
| JP | 2005-522266 A | 7/2005 |
| JP | 2006-506201 A | 2/2006 |
| JP | 2008-541832 A | 11/2008 |
| JP | 4673987 B2 | 4/2011 |
| WO | WO-88/00813 | 2/1988 |
| WO | WO-96/01591 | 1/1996 |
| WO | WO-97/26939 | 7/1997 |
| WO | WO-99/03404 | 1/1999 |
| WO | WO-99/05977 | 2/1999 |
| WO | WO-99/08607 | 2/1999 |
| WO | WO-99/08743 | 2/1999 |
| WO | WO-99/40873 A1 | 8/1999 |
| WO | WO-99/62432 | 12/1999 |
| WO | WO-00/57815 A1 | 10/2000 |
| WO | WO-01/93782 | 12/2001 |
| WO | WO-02/00139 | 1/2002 |
| WO | WO-02/071977 A2 | 9/2002 |
| WO | WO-03/037191 A1 | 5/2003 |
| WO | WO-2005/117718 | 12/2005 |
| WO | WO-2006/026744 | 3/2006 |
| WO | WO-2006/034166 A2 | 3/2006 |
| WO | WO-2006/052322 A2 | 5/2006 |
| WO | WO-2006/091891 A2 | 8/2006 |
| WO | WO-2006/119422 A2 | 11/2006 |
| WO | WO-2007/047851 A2 | 4/2007 |
| WO | WO-2007/076480 A2 | 7/2007 |
| WO | WO-2007/095031 A2 | 8/2007 |
| WO | WO-2007/121405 | 10/2007 |
| WO | WO-2008/022327 A2 | 2/2008 |
| WO | WO-2008/109228 A2 | 9/2008 |
| WO | WO-2008/151204 | 12/2008 |
| WO | WO-2008/157507 A2 | 12/2008 |
| WO | WO-2009/076515 | 6/2009 |
| WO | WO-2009/132045 A2 | 10/2009 |
| WO | WO-2009/134337 | 11/2009 |
| WO | WO-2009135166 A2 | 11/2009 |
| WO | WO-2010/030991 | 3/2010 |
| WO | WO-2010/147808 A1 | 12/2010 |
| WO | WO-2011/057002 A2 | 5/2011 |
| WO | WO-2011/057277 A2 | 5/2011 |
| WO | WO-2011/130081 | 10/2011 |
| WO | WO-2011/153304 | 12/2011 |
| WO | WO-2012/068175 A2 | 5/2012 |
| WO | WO-2012/112749 A2 | 8/2012 |
| WO | WO-2012/166804 A1 | 12/2012 |

OTHER PUBLICATIONS

U.S. Appl. No. 13/629,678, filed Sep. 28, 2012.
Hill, et al., "Initial Results of the AMPLATZER Vascular Plug in the Treatment of Congenital Heart Disease, Business Briefing," US Cardiology 2004.
Ronnen, "AMPLATZER Vascular Plug Case Study, Closure of Arteriovenous Fistula Between Deep Femoral Artery and Superficial Femoral Vein," AGA Medical Corporation, May 2007.
U.S. Appl. No. 13/669,652, filed Nov. 6, 2012.
U.S. Appl. No. 13/826,298, filed Mar. 14, 2013.
U.S. Appl. No. 13/795,556, filed Mar. 12, 2013.
U.S. Appl. No. 13/962,267, filed Aug. 8, 2013.

* cited by examiner ated. These tufts may be advantageous in device retention at an implant site.

MULTIPLE LAYER FILAMENTARY DEVICES FOR TREATMENT OF VASCULAR DEFECTS

CROSS REFERENCE TO RELATED APPLICATIONS

This filing is a continuation of U.S. patent application Ser. No. 12/911,034, filed Oct. 25, 2010 now U.S. Pat. No. 9,039,726, which is a continuation of U.S. patent application Ser. No. 12/427,620 filed Apr. 21, 2009 now U.S. Pat. No. 8,142,456 which claims the benefit of each of: U.S. Patent Application Ser. Nos. 61/046,594 and 61/046,670, both filed Apr. 21, 2008; U.S. Patent Application Ser. Nos. 61/083,957 and 61/083,961, both filed Jul. 28, 2008; and U.S. Patent Application Ser. No. 61/145,097, filed Jan. 15, 2009. Each of the foregoing applications is incorporated herein by reference in its entirety.

FIELD OF THE INVENTION

The present invention is directed to braid-balls suitable for aneurysm occlusion and/or parent vessel occlusion/sacrifice (e.g., in treating neurovascular defects).

BACKGROUND

Especially for aneurysm treatment, but also for either one of the aforementioned treatments, the form of the ball is very important. In particular, the density of the device is paramount in applications where braid itself is intended to moderate or stop blood flow—allowing thrombosis within a volume formed by the ball.

According to the present invention, braid-ball type implants are provided in braid of sufficient density is provided to moderate blood flow within the volume of the implant. Upon thrombosis, flow thereto is stopped. Alternatively, a blood-barrier covering can be applied to the filamentary structure to immediately stop blood flow into the vascular site, in which the implant volume is set.

In either case, to form thrombosis within the volume of the ball, the filaments of the braid matrix permit filling of the implant with blood when emplaced at a vascular treatment site. This blood then thromboses due to the flow-disruption effect(s).

Unlike Nitinol tube-cut cages that may be suitable for (or assist) in coil retention, the ball devices are adapted to work alone—or in combination with each other to effect a complete treatment. As such, high density braid/mesh is typically required. Namely, braid having at least about 48 ends, typically set at about 90 degrees or greater, in diameters from about 4 to about 8 mm may be employed. At larger diameters (e.g., about 6 to 12 or more), more wire ends (e.g., 64, 72 and upwards) may be employed in forming the balls.

Suitable braid for constructing the balls may be obtained from Secant Medical, Inc. Wire diameters may be in the range of about 0.001 to about 0.003 inches, depending on desired delivery profile (which is typically less than about 0.050 inches). The braid forming the balls may incorporate only one size wire, or may be formed with multiple sizes.

The wire is preferably superelastic NiTi alloy. The metal may be a binary alloy or a ternary alloy to provide additional radiopacity. Alternatively, radiopaque platinum fibers may be included in the braid, or the wire may comprise platinum or gold cord Nitinol DFT. Otherwise, wraps or bands (preferably Pt) used to secure the braid wire may serve as the sole radiopaque feature(s).

In any case, the construction approaches described herein enable producing these useful devices. Whether comprising braid alone, or incorporating some further blood-barrier covering (such as a thin urethane film as may be applied by Hantel, Inc. or others) the use of braid presents numerous challenges in managing the termination of multiple wires and in forming the desired structures.

Also included in the invention are detachable implant pushers that utilize a resistance wire heater to thermally sever a suture associated with the implant to effect release. As distinguished from known approaches where an implant is retained by a loop connected back to a delivery system pusher that is withdrawn with the devilry system, the present invention contemplates a leave-behind tether.

Further details, variations, modification and optional features of the invention may be appreciated by review of any of the incorporated patent applications. However, the priority date and subject matter included in the appended claims rely solely on the subject matter filed in U.S. Provisional Patent Application Nos. 61/046,670 and 61/046,594, the earliest patent applications (each filed Apr. 21, 2008) one which U.S. patent application Ser. No. 12/427,620 relies. Selected figures from the '670 and '594 application and all of text from the '594 application—all—incorporated by reference in the parent application hereto is reproduced herein.

DETAILED DESCRIPTION OF THE INVENTION

Implants

Referring to the figures, a filamentary implant 2 is formed out of braid to treat vascular sites. Interwoven filaments 4 form a braid matrix 6 that define a self-expandable occlusion device.

Figure 1:
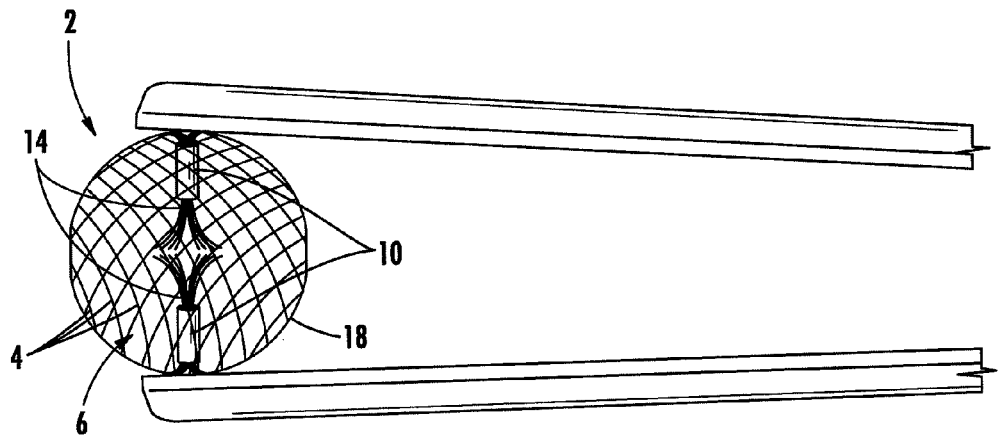
FIG. 1 is a photograph taken from U.S. Provisional Patent Application No. 61/046,670 (incorporated herein by reference) demonstrating actual reduction to practice of a single-layer braid ball device made according to the present invention.
Figure 2A:
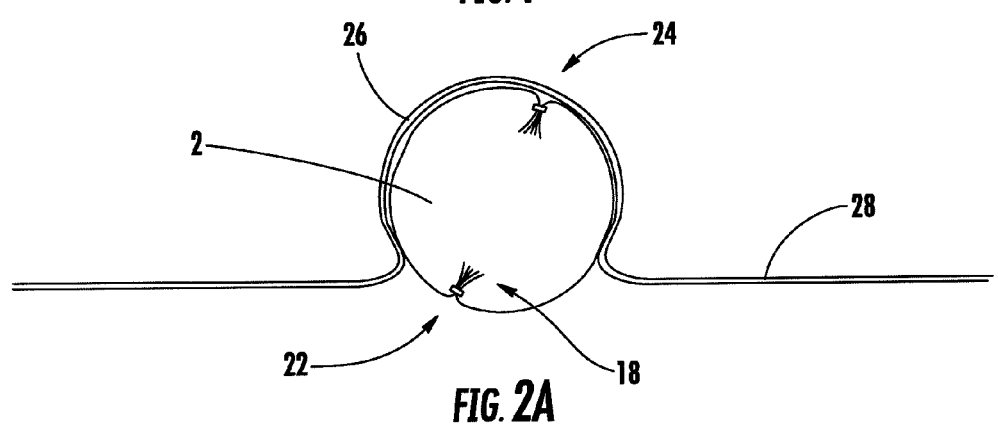
FIGS. 2A and 2B are side-sectional views of the braid ball in isolation and in use, respectively.
Figure 2B:
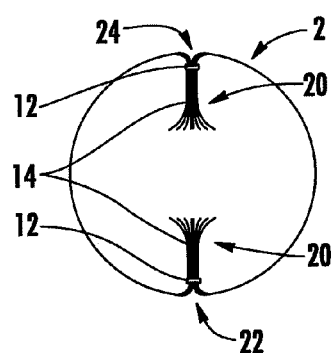

As single layer of the braid is provided in which ends of the braid are secured and managed to provide an atraumatic interface. Specifically, ties 10 (as illustrated in FIG. 1) or bands 12 (as illustrated in FIGS. 2A and 2B) secure filament the ends 14 of the braid from which the implant is constructed.

In the implant variation pictured, the expanded configuration defines an ovoid or roughly spherical shell 18 that is permeable to blood. The braid defining the proximal and distal ends of the implant turns or curves inward to a point where it is secured within the periphery of the shell.

The inversion of the braid provides recessed securement of the braid resulting in atraumatic ends of the implant. The braid filaments optionally extend beyond the securing/securement features in order to define wire filament "tufts" 20 that will further promote thrombosis of blood that enters the ball upon deployment within a patient's vasculature. However configured in regard to braid filament end securement and termination, inset ends of the braid (proximal and distal insets 22/24, respectively) are demonstrated when the implant is in an expanded state to fill an aneurysm 26 off of a vessel 28.

Delivery Systems

Figure 3:
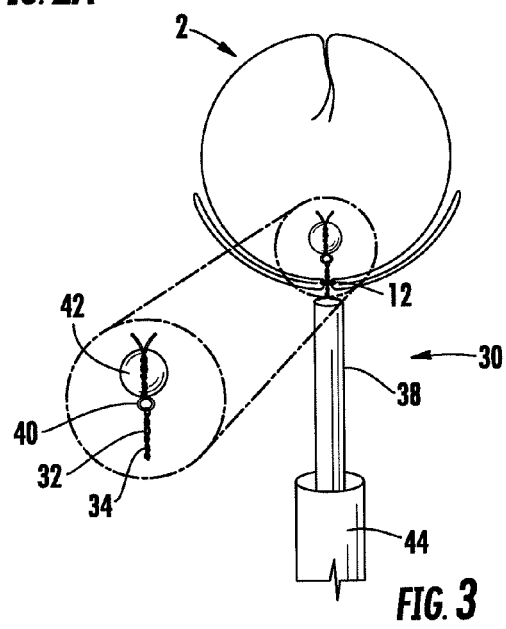
FIG. 3 illustrates a suture-melt resistance heater pusher for implant delivery.

FIG. 3 illustrates a detachable catheter/pusher 30, optionally, for use in the present invention. Generally, it includes a resistance wire bridge 32 across insulated conductors 34 (a typical construction). What is unique is that the conductor wires are twinned/twisted along a length of the delivery pusher shaft 38 as shown. This configuration alleviates bending bias/preference. Upon application of voltage, the tip thermally severs the polymer filament (e.g., suture 40) in contact therewith. At least the suture portion is received within the implant 2 (e.g., passing through a braid-securing band 12). The suture is retained in/with the implant upon actuation to release the implant by cutting through the suture with heat. A ball stop 42 that is tied to the suture retains the filament in/with the implant is also illustrated. Finally, pusher 30 is shown received within a typical microcatheter 44 for vascular access, after passage therethough. Note also, other advantageous delivery system are referenced and described in the incorporated patent application.

Methods of Manufacture

Included in the intention is a method of manufacture including tying-off or otherwise securing a second end of a braid within an interior volume of a ball where other approaches would be impracticable. The technique may be employed in creating the balls (be they spherical or ovaloid in cross-section, etc.) out of one continuous section of braid. In so doing, joints and other delivery profile-increasing features are avoided—as well as potential areas for failure. Accordingly, the subject implants are extremely robust and fully recoverable to their aneurysmal shape as is required when they are delivered through a catheter in low profile. Robust shape recovery is required in treatments targeting distal vasculature, especially the tortuous neurovasculature encountered in human brains.

Figure 4A:
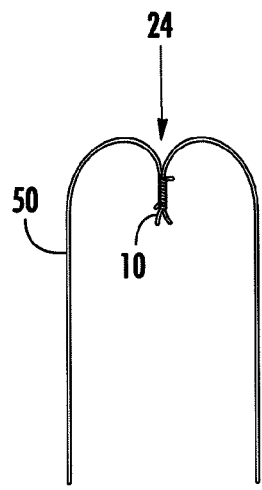
FIGS. 4A-4F illustrate a production path of one implant embodiment encompassed by the current invention.
Figure 4B:
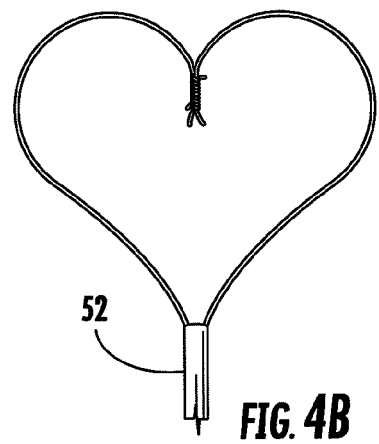
Figure 4C:
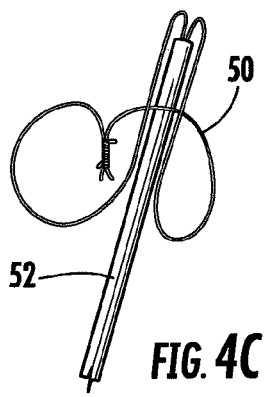
Figure 4D:
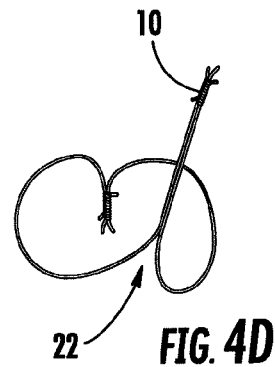
Figure 4E:
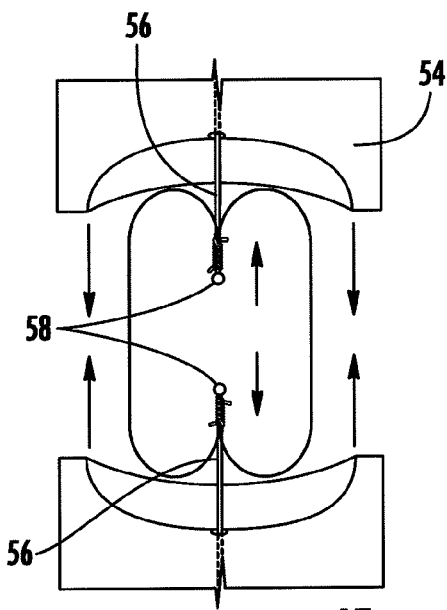
Figure 4F:
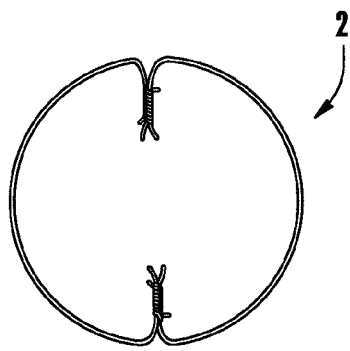

A detailed example of one process path for implant formation is illustrated in FIGS. 4A-4F. As shown in FIG. 4F an final implant 2 may begin as a section 50 of braided material. The tubular braid stock is secured. As shown, it is tied-off with a wire wrap 10. Such action develops an inset region 24 for the implant body. An opposite end of the braid is then captured in a transfer tube 52. The tube is passed through the volume of the implant and secured with a second tie 10 at the other side.

Additional refinement to the shape over that shown in FIG. 4E may be imparted within a shape-setting form 54. Mandrels 56 including stops 58 received through the securement features may be employed to force apposition of the ball to the shape of the form when pulled apart as indicated by arrows. After shape-setting in the form (as appropriate to the selected material—e.g., as in heat setting superelastic Nitinol) the mandrels are removed and the implant shaping is complete as shown in FIG. 4F. However, these additional forming steps are not necessary given that (in point of fact) the implant in FIG. 1 was produced without employing the same.

Figure 5A:
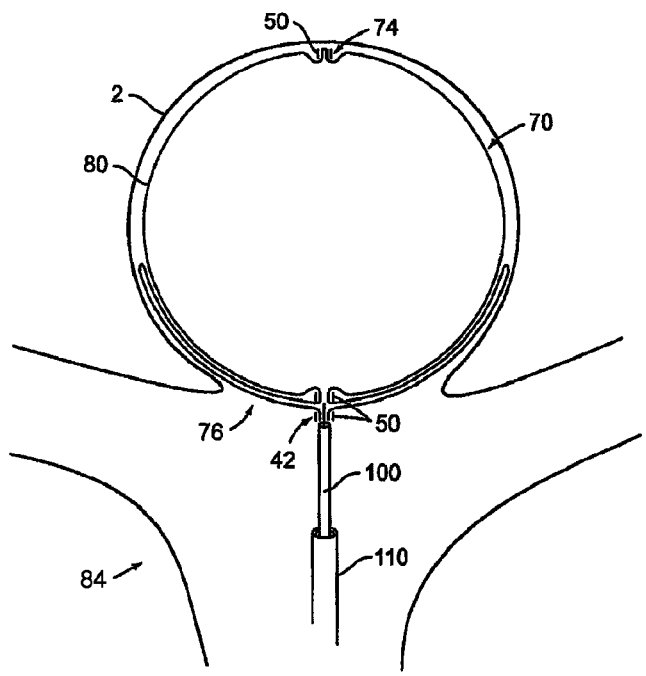
FIGS. 5A and 5B are side-sectional views illustrating proximal-flap braid ball implant variations deployed within bifurcation aneurysm locations.
Figure 5B:
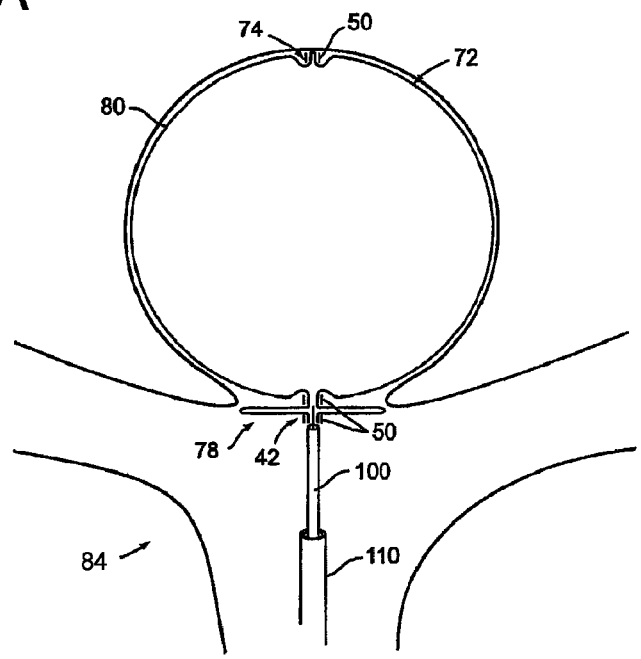

The implants 70, 72 shown in FIGS. 5A and 5B, respectively, may also be dual layer construction. In which case, they would share their distal configuration with the previous implants 20/40/60 shown in FIGS. 1A-3C of U.S. patent application Ser. No. 12/427,620, filed on Apr. 21, 2009. As shown, they are single-layer devices in which the distal end takes the form of an inset hub 74.

Either way, the implants include unique proximal-end configurations. In addition to a ball or bulbous portion 80, each implant includes a flap 76, 78 intended to improve its blood flow disruption potential. Flap 76 included in implant 70 is intended for intra-aneurysmal use. To deliver it as shown, the ball or bulbous portion is first delivered into the aneurysm sac 2. Then, that portion of the device is compressed while still mounted to pusher 100 to deploy the flap section therein. After final positioning is achieved as shown in FIG. 5A, then the pusher locking member(s) received within hub 42 are released. Finally, the pusher is withdrawn into the delivery catheter 110. To assist in the delivery method, one or more additional radiopaque features (such as a band 50 at the proximal end of ball section 80) may be provided so that deployment can be visualized at each stage.

The implant in FIG. 5B requires no such complication in delivery. Because flap 78 is of a size selected only to fill the aneurysm neck, it can be delivered straight-away. Still, intermediate radiopaque features may be desirable to confirm appropriate fit and/or deployment.

As pictured, the ball-and-disk variation of the implant shown in FIG. 5B may only be applicable to smaller-neck aneurysms as compared to the FIG. 5A "acorn" type variation. Generally, the size of the disc will not be significantly larger than the parent/trunk vessel 6 diameter and or that of the bifurcation region 84. Otherwise, the vasculature will interfere with deployment. As such, the disk may be limited to about 2.5 to about 5 mm in diameter.

While understood better in the context of the implant manufacture steps below, flap 78 may be formed using a simple washer or plate over which the braid is heat set. Otherwise, the forming tool may be curved or dished so that flap 78 better follows the contour of the main implant body.

Flap 76 in the FIG. 5A variation will typically be formed using a concave/convex form in similar fashion. The size of this flap may vary. As shown, its outer extent is roughly the same diameter of the ball portion 80 of the device. It may be smaller and/or cover a lesser extent of the proximal side of implant 70. Generally, flap 76 will cover at least about a third and as much as one-half of body 80. In this way, adequate neck coverage is better insured when employed to treat wide-neck aneurysms.

Methods of Use

Any one of the subject implants is delivered to a target site employing known percutaneous catheter access techniques. The implant may be secured to a pusher (e.g., pusher 30) used to advance it through the access catheter (e.g., microcatheter 44). Upon emplacement at the treatment site (e.g., cerebral aneurysm 26 as illustrated in FIG. 2A), the implant can be detached. With the exemplary system shown in FIG. 3, the suture 40 passing through the proximal end of the implant 2 is severed by melting it using a resistance heater. This retention/release fiber remains in and with the implant.

The invention claimed is:

1. A method of treating a patient, comprising:
   providing a device for treatment of a patient's vasculature, comprising:
   a self-expanding resilient permeable shell having a proximal end, a distal end, a longitudinal axis and further including a plurality of elongate resilient filaments with a woven structure secured relative to each other at proximal ends and distal ends thereof, a radially constrained elongated state configured for delivery within a microcatheter, and an expanded relaxed state with a globular configuration relative to the radially constrained elongated state, and an inner structure of filamentary members disposed within an interior volume of the resilient permeable shell and secured to the permeable shell at an end thereof, the inner structure including a plurality of elongate resilient filaments with a woven structure secured relative to each other at least at the proximal ends thereof, which has a radially constrained elongated state which is shorter than the permeable shell in its radially constrained state and which has an expanded relaxed state relative to the radially constrained state;

advancing the device to a treatment site within a patient's vasculature in a constrained elongated state; and deploying the device within a vascular defect at the treatment site within the patient's vasculature such that the permeable shell and inner structure self-expand to their respective expanded states.

2. The method of claim 1, wherein the filaments of at least one of either the permeable shell or the inner structure comprise at least two different transverse dimensions.

3. A self-expanding implant for treating a patient's vasculature, the implant comprising:

a resilient, permeable shell having proximal and distal end portions, an interior volume, a longitudinal axis, and a plurality of elongate, woven filaments secured relative to each other at proximal end portions and distal end portions thereof, the shell having a radially constrained, elongated state configured for delivery within a microcatheter and an expanded state relative to its radially constrained, elongated state; and an inner structure, disposed within the shell interior volume, comprising a plurality of elongate, woven filaments and being secured to the shell at the proximal end portion thereof, the inner structure having a radially constrained, elongated state shorter than the radially constrained, elongated state of the shell, the inner structure having an expanded state relative to its radially constrained, elongated state, wherein when the shell and the inner structure self-expand to their respective expanded states, a free, unsecured end portion of the inner structure is longitudinally separated from an inner surface of the shell distal end portion by an internal gap.

4. The device of claim 3, wherein the inner structure filaments are secured at the distal end portion thereof to form an inner hub.

5. The device of claim 3, wherein filaments of the inner structure comprise a woven structure forming a substantially enclosed volume.

6. The device of claim 3, wherein the proximal and distal end portions comprise respective proximal and distal hubs, the proximal and distal hubs being disposed exterior to the interior volume and being inset into the interior volume.

7. An embolic device for treatment a patient's vasculature, the device comprising:

a braided structure having an interior volume and comprising a plurality of wires that are secured relative to each other at proximal and distal end portions of the structure to form respective proximal and distal hubs, the proximal and distal hubs disposed exterior to the interior volume and being inset into the interior volume, the structure being adapted to (i) compress into a compressed state, in which the proximal and distal hubs are longitudinally separated at a first distance, for delivery through a microcatheter and (ii) self-expand into an expanded shape, in which the proximal and distal hubs are longitudinally separated at a second distance, less than the first distance, upon release from constraint.

8. The embolic device of claim 7, wherein the expanded shape comprises a globular shape.

9. The embolic device of claim 7, wherein the braided structure comprises a single layer.

10. The embolic device of claim 7, wherein the braided structure comprises inner and outer layers.

11. The embolic device of claim 10, wherein a distal end portion of the inner layer is spaced apart from a distal end portion of the outer layer.

12. The embolic device of claim 11, wherein filaments of the inner layer converge to an unsecured, inner hub to form an inner structure, and wherein filaments of the outer layer converge to the distal hub, the inner hub being spaced apart from the distal hub along a longitudinal axis of the device.

13. The embolic device of claim 12, wherein the inner structure and the outer layer meet at the proximal hub.

* * * * *